United States Patent [19]

Walser

[11] 4,118,386
[45] Oct. 3, 1978

[54] SYNTHESIS OF IMIDAZO[1,5-a]DIAZEPINE-3-CARBOXY-LATES

[75] Inventor: Armin Walser, West Caldwell, N.J.

[73] Assignee: Hoffmann-La Roche Inc., Nutley, N.J.

[21] Appl. No.: 784,187

[22] Filed: Apr. 4, 1977

[51] Int. Cl.² .............. C07D 210/00; C07D 211/02; C07D 487/04
[52] U.S. Cl. .................. 260/239.3 T; 260/294.8 B; 260/295 T; 548/324
[58] Field of Search .................. 548/324; 260/295 T, 260/294.8 B, 294.9, 239.3 T

[56] References Cited
U.S. PATENT DOCUMENTS 2,984,666   5/1961   Bortnick et al. .................. 548/324
3,920,687   11/1975  Buzby et al. .................... 548/324

Primary Examiner—Henry R. Jiles
Assistant Examiner—Cary Owens
Attorney, Agent, or Firm—Samuel L. Welt; George M. Gould; Frank P. Hoffman

[57] ABSTRACT

A process to produce diazepine-3-carboxylates of the formula

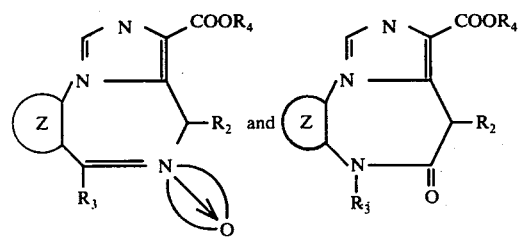

-continued wherein 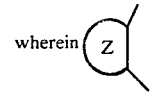

is selected from the group consisting of

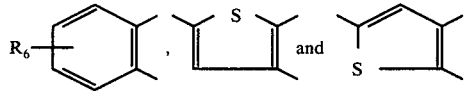

$R_6$ is selected from the group consisting of hydrogen, halogen, nitro, cyano, trifluoromethyl, lower alkyl, and lower alkanoyl;

$R_4$ is lower alkyl; $R_3$ is selected from the group consisting of phenyl, mono-substituted phenyl, disubstituted phenyl, pyridyl and mono-substituted pyridyl; and $R_2$ is hydrogen or lower alkyl which comprises reacting a compound of the formula

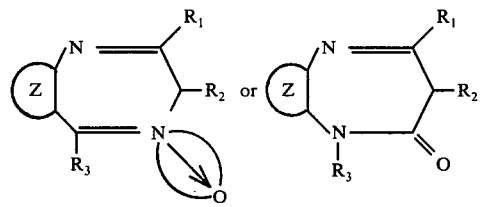

wherein $R_1$ is of the formula

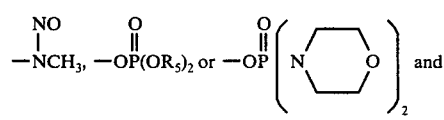

$R_5$ is lower alkyl with a compound of the formula

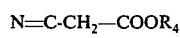

in the presence of a base sufficiently strong to generate the anion of the isocyanoacetate.

3 Claims, No Drawings ized
SYNTHESIS OF IMIDAZO[1,5-a]DIAZEPINE-3-CARBOXYLATES

DESCRIPTION OF THE INVENTION

The present invention relates to a process to produce compounds of the formula

[Structures I and II shown]

wherein Z is selected from the group consisting of

[Three ring structures shown with $R_6$ substituent]

$R_6$ is selected from the group consisting of hydrogen halogen, nitro, cyano, trifluoromethyl, lower alkyl, and lower alkanoyl; $R_4$ is lower alkyl; $R_3$ is selected from the group consisting of phenyl, mono-substituted phenyl, disubstituted phenyl, pyridyl and mono-substituted pyridyl; and $R_2$ is hydrogen or lower alkyl which comprises reacting a compound of the formula

[Structures III and IV shown]

wherein $R_1$ is the formula $$-NCH_3(NO), -OP(OR_5)_2(O), \text{ or } -OP(O)(N\text{-morpholino})_2$$

$R_5$ is lower alkyl, with a compound of the formula $$N{\equiv}C-CH_2-COOR_4 \qquad V$$

in the presence of a base sufficiently strong to generate the anion of the isocyanoacetate.

The end products of the subject process are compounds having pharmacological utility as muscle relaxants, sedatives, anxiolytics and anti-convulsants and are intermediates for the preparation of compounds having such activity.

The starting materials of the formula III and IV are known or methods for their preparation are provided herein. Compounds of formula III wherein $R_1$ is $$-NCH_3(NO) \text{ and } -OP(O)(N\text{-morpholino})_2$$

are disclosed along with methods for their preparation in Belgian Pat. No. 833,248 issued Mar. 3, 1976. Compounds of formula IV wherein $R_1$ is $$-NCH_3(NO) \text{ and } -OP(O)(N\text{-morpholino})_2$$

are disclosed along with methods for their preparation in U.S. Pat. No. 4,080,323 issued on Mar. 21, 1978 for example.

Other leaving groups may be utilized beside the three $R_1$-substituents disclosed above, for example, chloro may also be utilized. Compounds of formula III wherein $R_1$ is —Cl are disclosed along with methods for their preparation in German Offenlegungschrift No. 2,404,736 published on Aug. 14, 1975 for example.

Compounds of formula III or IV wherein $R_1$ is $$-OP(O)(OR_5)_2$$

are produced by the reaction of the corresponding diazepin-2-one or dione with a base sufficiently strong enough to generate the anion of the lactam and thereafter reaction with a dialkyl chlorophosphate in an inert solvent such as dimethylformamide, hexamethyl phosphoramide, dimethyl sulfoxide, tetrahydrofuran or any other suitable organic solvent. All that is required of the organic solvent in the above step (as well as any subsequent step) is that the starting materials be soluble therein and that the solvent does not interfere with the ensuing reaction. The reaction temperature may range from about $-40°$ C. to about room temperature with about $0°$ C. as a preferred temperature. The compound of formula III or IV wherein $R_1$ is of the formula $$-OP(O)(OR_5)_2$$

wherein $R_5$ is lower alkyl may or may not be isolated from the above reaction. The novel process may be carried out in situ utilizing the solvents and the same or a different base as utilized in the previous reaction.

The novel process of the present invention consists of the reaction of a compound of the formulas III or IV with a compound of the formula V, i.e., a lower alkyl isocyanoacetate, preferably ethyl.

As used in this disclosure, the term "lower alkyl" or "alkyl" comprehends both straight and branched chain ($C_1$–$C_7$) carbon-hydrogen radicals, preferably $C_1$–$C_4$ carbon-hydrogen radicals such as methyl, ethyl, propyl, isopropyl, butyl and the like.

By the term "lower alkanoyl" as utilized herein, an acyl moiety of a $C_1$–$C_7$ preferably a $C_1$–$C_4$ alkanoic acid is intended, e.g., acetyl, propionyl, butyryl and the like, i.e., moieties of the formula

wherein R is $C_1$–$C_6$ or hydrogen. Also as utilized herein, the term "lower alkanoyl" comprehends a protected ketone such as an acetal or ketal having 2 to 7 carbon atoms, e.g. a group of the formula

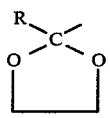

wherein R is $C_1$–$C_6$ or hydrogen. The ketal or aldehyde protecting group is utilized to prevent conversion of the contained ketone or aldehyde in oxidation, reduction and condensation reactions.

The term "halogen" is used to include all four forms thereof, i.e., chlorine, bromine, fluorine and iodine.

The $R_3$ phenyl moiety may be mono- or di-substituted provided that such di-substitution occurs in the 2,3; 2,5; or most preferably, in the 2,6-position of the phenyl moiety. Suitable mono-substituents include halogen and nitro and preferably are substituted in the 2-position of the phenyl moiety. Suitable di-substituents are 2,6 or 2,5 di-halogen and 2,6 or 2,5 halogen-nitro. In the case of mono-substituted pyridyl, suitable substituents include halogen and nitro.

In the case wherein $R_2$ is a lower alkyl substituent, optical isomerism will occur and such optical antipodes and racemates are within the ambit of this invention.

Bases strong enough to form the anion of the isocyanoacetate include alkali metal alkoxides, such as, potassium tertiary butoxide or sodium methoxide and alkali metal hydrides, such as sodium hydride and alkali metal amides, such as lithium amide or lithium diisopropylamide.

The following examples are illustrative of the scope of the present invention. The temperatures are given in degrees centigrade unless otherwise indicated.

EXAMPLE 1

Ethyl 8-Chloro-6-(2-chlorophenyl)-4H-imidazo[1,5-a][1,4]benzodiazepine-3-carboxylate A mixture of 1.41 g (0.0125 mole) of ethyl isocyanoacetate, 1.4 g (0.0125 mole) of potassium t-butoxide and 125 ml of tetrahydrofuran was stirred at room temperature for 10 minutes. Following the addition of 5.23 g (0.01 mole) of 7-chloro-5-(2-chlorophenyl)-2-[bis(morpholino)-phosphinyloxy]-3H-1,4-benzodiazepine stirring was continued for ½ hr. The reaction mixture was acidified with glacial acetic acid, diluted with 250 ml of water and extracted with three 100 ml portions of methylene chloride. The methylene chloride extracts were washed with saturated sodium bicarbonate solution, dried and evaporated. The crystalline residue was collected and washed with ether to give product with mp 215°–220°. The material was recrystallized from methylene chloride/ethyl acetate for analysis, mp 225°–228°.

Anal. Calcd for $C_{20}H_{15}Cl_2N_3O_2$: C, 60.02; H, 3.78; N, 10.50.

Found: C, 50.97; H, 3.77; N, 10.31.

Belgian Pat. No. 833,249, issued Mar. 10, 1976.

EXAMPLE 2

8-Chloro-6-(2-fluorophenyl)-4H-imidazo[1,5-a][1,4]benzodiazepine-3-carboxylic acid, ethyl ester Potassium t-butoxide, 1.4 g (0.0125 mole), was added to a solution of 1.4 g (0.0124 mole) of ethyl isocyanoacetate in 125 ml of dry tetrahydrofuran. After stirring under argon for 10 minutes, 5.07 g (0.01 mole) of 7-chloro-2-[bis(morpholino)-phosphinyloxy]-5-(2-fluorophenyl)-3H-1,4-benzodiazepine was added and stirring was continued for 30 minutes at room temperature. The reaction mixture was then acidified with glacial acetic acid, diluted with water and extracted with methylene chloride. The extracts were washed with saturated sodium bicarbonate solution, dried and evaporated. Crystallization of the residue from ether yielded crystals which were recrystallized from methylene chloride/ether/hexane for analysis, mp 195°–196°.

Anal. Calcd for $C_{20}H_{15}ClFN_3O_2$: C, 62.59; H, 3.94; N, 10.95.

Found: C, 62.59; H, 3.73; N, 11.01

EXAMPLE 3

6-(2-Chlorophenyl)-8-nitro-4H-imidazo[1,5-a][1,4]benzodiazepine-3-carboxylic acid, ethyl ester 5-(2-Chlorophenyl)-2-[bis(morpholino)-phosphinyloxy]-8-nitro-3H-1,4-benzodiazepine, 21.2 g (0.04 mole) was added to a mixture of 5.6 g (0.05 mol) of potassium t-butoxide, 5.6 g (0.05 mole) of ethyl isocyanoacetate and 500 ml of dry tetrahydrofuran. After stirring for 30 minutes under argon at room temperature, the reaction mixture was acidified with acetic acid, diluted with water and extracted with methylene chloride. The extracts were washed with saturated sodium bicarbonate solution, dried and evaporated. Crystallization of the residue from ethyl acetate yielded yellowish product which was recrystallized from methylene chloride/ethanol to give off-white crystals with mp 250°–252°.

Anal. Calcd for $C_{20}H_{15}ClN_4O_4$: C, 58.47; H, 3.68; N, 13.63.

Found: C, 58.69; H, 3.56; N, 13.72.

EXAMPLE 4

8-Chloro-6-phenyl-4H-imidazo[1,5-a][1,4]benzodiazepine-5-oxide-3-carboxylic acid, ethyl ester Potassium t-butoxide, 1.40 g (0.0125 mole) was added to a stirred solution of 1.41 g (0.0125 mole) of ethyl isocyanoacetate in 125 ml of tetrahydrofuran under a nitrogen atmosphere. After stirring for 10 minutes, 3.28 g (0.01 mole) of 7-chloro-2-(N-nitrosomethylamino)-5-phenyl-3H-1,4-benzodiazepine-4-oxide was added, and the stirring was continued for ½ hour. The mixture was acidified with galcial acetic acid and diluted with 300 ml of water. The crystals were collected and washed with water. Recrystallization from methylene chloride/ethyl acetate yielded colorless prisms with mp 292°–294°.

A. Walser et al., J. Heterocyclic Chem., 11, 619, (1974)

EXAMPLE 5

8-Chloro-6-(2-fluorophenyl)-4H-imidazo[1,5-a][1,4]benzodiazepine-3-carboxylic acid, ethyl ester Potassium t-butoxide, 1.29 g (0.0115 mol) was added to a stirred solution of 2.88 g (0.01 mol) of 7-chloro-1,3-dihydro-5-(2-fluorophenyl)-2H-1,4-benzodiazepine- 2-one in 50 ml of tetrahydrofuran, that had been cooled in an ice bath and covered with a nitrogen atmosphere. After stirring for 5 minutes, 2.59 g (0.015 mol) diethyl chlorophosphate was added. After stirring for 5 minutes, a mixture of 2.26 g (0.02 mol) of ethyl isocyanoacetate in 50 ml of tetrahydrofuran that had been treated with 2.24 g (0.02 mol) of potassium t-butoxide just prior to the addition, was added. After 5 minutes, the ice bath was removed and the stirring was continued for 15 minutes. The mixture was acidified with 2 ml of glacial acetic acid, diluted with 200 ml of saturated sodium bicarbonate solution and extracted twice with 125 ml portions of toluene. The extracts were dried and evaporated and the residue was crystallized from ether to give the product with mp 195°–197°. For analysis, the material was recrystallized from methylene chloride/ether/hexane to give colorless crystals with mp 195°–196°.

Anal. Calcd for $C_{20}H_{15}ClFN_3O_2$: C, 62.59; H, 3.94; N, 10.95.

Found: C, 62.59; H, 3.73; N, 11.01.

EXAMPLE 6

8-Bromo-6-(2-pyridyl)-4H-imidazo[1,5-a][1,4]benzodiazepine-3-carboxylic acid, ethyl ester A solution of 15.8 g (0.05 mol) of 7-bromo-1,3-dihydro-5-(2-pyridyl)-2H-1,4-benzodiazepin-2-one in 300 ml of dry tetrahydrofuran was cooled to 10° with stirring under argon. Potassium tert. butoxide 6.3 g (0.056 mol) was added and stirring was continued for 10 min. Following the addition of 14 ml of diethyl chlorophosphate the mixture was stirred for additional 20 min. A previously prepared mixture of 11.3 g ethyl isocyanoacetate, 11.3 g of potassium tert. butoxide and 300 ml of tetrahydrofuran was then poured into the reaction mixture.

The ice-water bath was removed and stirring was continued for 20 min at room temperature. After acidifying with acetic acid the mixture was diluted with 300 ml of saturated sodium bicarbonate solution and was extracted with 500 ml of toluene. The organic layer was washed with water, dried over sodium sulfate and evaporated. Crystallization of the residue from ether yielded the end product which was recrystallized from methylene chloride/ethanol and again from ethanol for analysis, mp 224°–225°.

Anal. Calcd for $C_{19}H_{15}BrN_4O_2$: C, 55.49; H, 3.68; N, 13.62.

Found: C, 55.38; H, 3.72; N, 13.63.

EXAMPLE 7

8-Iodo-6-(2-fluorophenyl)-4H-imidazo[1,5-a][1,4]benzodiazepine-3-carboxylic acid, ethyl ester A stirred solution of 3.8 g (0.01 mol) of 7-iodo-1,3-dihydro-5-(2-fluorophenyl)-2H-1,4-benzodiazepine-2-one in 50 ml of dimethyl formamide was cooled in an ice bath under an atmosphere of nitrogen. Potassium t-butoxide, 1.29 g (0.0115 mol) was added and after stirring for 5 minutes, 2.59 g (0.015 mol) of diethyl chlorophosphate was added and the stirring was continued for 5 minutes. A mixture of 2.26 g (0.02 mol) of ethyl isocyanoacetate in 50 ml of dimethylformamide that had been treated with 2.24 g (0.02 mol) of potassium t-butoxide just prior to the addition, was then added. After 5 minutes the ice bath was removed and the stirring was continued for 3 hours. The mixture was acidified with 2 ml of glacial acetic acid, diluted with 200 ml of saturated sodium bicarbonate solution and extracted with two 125 ml portions of toluene which were dried and evaporated. The residue was crystallized from ethyl acetate. For analysis, the crude product was chromatographed over silica gel using methylene chloride/ethyl acetate 1:1 (v/v) and then crystallized from ethyl acetate/hexane to give pure product with mp 200°–202°.

Anal. Calcd for $C_{20}H_{15}FIN_3O_2$: C, 50.54; H, 3.18; N, 8.84.

Found: C, 50.73; H, 3.19; N, 8.62.

EXAMPLE 8

8-Nitro-6-(2-fluorophenyl)-4H-imidazo[1,5-a][1,4]benzodiazepine-3-carboxylic acid, ethyl ester A stirred solution of 2.99 g (0.01 mol) of 7-nitro-1,3-dihydro-5-(2-fluorophenyl)-2H-1,4-benzodiazepin-2-one in 50 ml of tetrahydrofuran was cooled in an ice bath under an atmosphere of nitrogen. Potassium t-butoxide, 1.29 g (0.0115 mol) was added, and after stirring for 5 minutes, 2.59 g (0.015 mol) of diethyl chlorophosphate was added and the stirring was continued for an additional 5 minutes. A mixture of 2.26 g (0.02 mol) of ethyl isocyanoacetate in 50 ml of tetrahydrofuran that has been treated with 2.24 g (0.02 mol) of potassium t-butoxide, just prior to the addition, was then added. After 5 min, the ice bath was removed and the stirring was continued for 1 hour. The mixture was acidified with 2 ml of glacial acetic acid, diluted with 200 ml of saturated sodium bicarbonate solution and extracted with two 125 ml portions of toluene which were dried and evaporated. Crystallization from ethyl acetate yielded end product with mp 228°–231°. For analysis, the material was chromatographed over a column of 60 g of silica gel using ethyl acetate/methylene chloride 1:1 (v/v) and recrystallized from ethyl acetate/ether to give colorless crystals with mp 229°–232°.

Anal. Calcd for $C_{20}H_{15}N_4O_4$: C, 60.91; H, 3.83; N, 14.21.

Found: C, 61.14; H, 3.85; N, 14.30.

EXAMPLE 9

8-Chloro-4,6-dihydro-6-phenyl-5H-imidazo[1,5-a][1,5]benzodiazepin-5-one-3-carboxylic acid, ethyl ester Potassium t-butoxide, 0.14 g (1.25 mmol) was added to a stirred solution of 0.14 g (1.25 mmol) of ethyl isocyanoacetate in 25 ml of tetrahydrofuran. The mixture was stirred for 5 minutes under a nitrogen atmosphere and then 0.328 g (1 mmole) of 7-chloro-3,5-dihydro-2-(N-nitrosomethylamino)-5-phenyl-4H-1,5-benzodiazepin-4-one was added. The mixture was stirred for 1 hour at room temperature and was then acidified with glacial acetic acid, diluted with 25 ml of saturated sodium bicarbonate solution and extracted twice with 100 ml of methylene chloride which was dried and evaporated. The residue was crystallized with ethyl acetate/ether to yield an end product with mp 252°–255°. Recrystallization for analysis from methylene chloride/ethyl acetate gave colorless crystals with mp 256°–258°.

Anal. Calcd for $C_{20}H_{16}ClN_3O_3$: C, 62.92; H, 4.22; N, 11.01.

Found: C, 62.72; H, 4.02; N, 10.92.

What is claimed is:

1. A process to produce diazepine-3-carboxylates of the formula

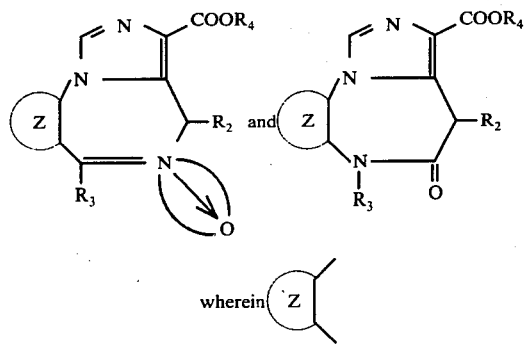

wherein 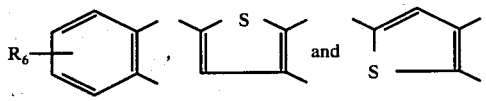

is selected from the group consisting of

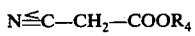

$R_6$ is selected from the group consisting of hydrogen, halogen, nitro, cyano, trifluormethyl, lower alkyl, and lower alkanoyl; $R_4$ is lower alkyl; $R_3$ is selected from the group consisting of phenyl, halo or nitro mono-substituted phenyl, halo or nitro disubstituted phenyl, pyridyl and halo or nitro mono-substituted pyridyl; and $R_2$ is hydrogen or lower alkyl which comprises a compound of the formula

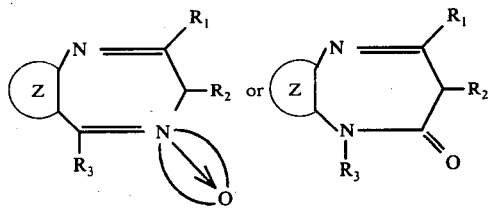

wherein $R_1$ is of the formula $$-\underset{\underset{CH_3}{|}}{N}O, \quad -O\overset{O}{\underset{\|}{P}}(OR_5)_2 \text{ or } -O\overset{O}{\underset{\|}{P}}\left(N\underset{\phantom{N}}{\diagdown}O\right)_2 \text{ and}$$

and $R_5$ is lower alkyl with a compound of the formula $$N\equiv C-CH_2-COOR_4$$

in the presence of a base sufficiently strong to generate the anion of the isocyanoacetate.

2. The process of claim 1 wherein $R_4$ is ethyl.

3. The process of claim 1 wherein the base is selected from the group consisting of alkali metal alkoxides, alkali metal hydrides and alkali metal amides.

* * * * *